United States Patent
Fenner et al.

(10) Patent No.: US 7,167,074 B2
(45) Date of Patent: Jan. 23, 2007

(54) INTEGRATED PLANAR FLYBACK TRANSFORMER

(75) Inventors: Andreas A. Fenner, Chandler, AZ (US); John V. Anderson, II, Mesa, AZ (US); Mohsen Askarinya, Chandler, AZ (US); Tina F. Abnoosi, Paradise Valley, AZ (US)

(73) Assignee: Medtronic, Inc., Minneapolis, MN (US)

( * ) Notice: Subject to any disclaimer, the term of this patent is extended or adjusted under 35 U.S.C. 154(b) by 0 days.

(21) Appl. No.: 11/034,323

(22) Filed: Jan. 12, 2005

(65) Prior Publication Data

US 2006/0152326 A1    Jul. 13, 2006

(51) Int. Cl.
*H01F 5/00* (2006.01)

(52) U.S. Cl. ............................ 336/200; 336/223; 607/5
(58) Field of Classification Search ................ 336/200, 336/223, 232; 607/5
See application file for complete search history.

(56) References Cited

U.S. PATENT DOCUMENTS

| | | | |
|---|---|---|---|
| 4,024,452 A | 5/1977 | Seidel | 321/2 |
| 4,465,979 A | 8/1984 | Russo | 330/66 |
| 4,803,609 A | 2/1989 | Gillett et al. | 363/17 |
| 4,816,784 A | 3/1989 | Rabjohn | 333/24 R |
| 4,977,491 A | 12/1990 | Domenget et al. | 363/15 |
| 5,010,314 A | 4/1991 | Estrov | 336/198 |
| 5,341,281 A | 8/1994 | Skibinski | 363/39 |
| 5,353,001 A | 10/1994 | Meinel et al. | 336/83 |
| 5,430,424 A | 7/1995 | Sato et al. | 336/200 |
| 5,598,327 A | 1/1997 | Somerville et al. | 363/131 |
| 5,657,942 A | 8/1997 | Faulk | 242/443.1 |
| 5,716,713 A | 2/1998 | Zsamboky et al. | 428/457 |
| 5,719,545 A | 2/1998 | Johnson | 336/180 |
| 5,754,088 A | 5/1998 | Fletcher et al. | 336/200 |
| 5,781,077 A | 7/1998 | Leitch et al. | 332/117 |
| 5,781,093 A | 7/1998 | Grandmont et al. | 336/232 |
| 5,844,461 A | 12/1998 | Faulk et al. | 336/206 |
| 5,889,660 A | 3/1999 | Taranowski et al. | 363/19 |
| 5,949,321 A | 9/1999 | Grandmont et al. | 336/232 |
| 6,069,548 A | 5/2000 | Baarman et al. | 336/65 |
| 6,124,778 A * | 9/2000 | Rowley et al. | 336/200 |
| 6,144,276 A | 11/2000 | Booth | 336/61 |
| 6,211,767 B1 | 4/2001 | Jitaru | 336/200 |
| 6,222,733 B1 | 4/2001 | Gammenthaler | 361/705 |
| 6,278,354 B1 | 8/2001 | Booth | 336/200 |
| 6,307,457 B1 | 10/2001 | Wissink et al. | 336/200 |
| 6,320,490 B1 | 11/2001 | Clayton | 336/180 |
| 6,420,952 B1 | 7/2002 | Redilla | 336/84 M |
| 6,477,414 B1 * | 11/2002 | Silvian | 607/5 |
| 6,570,250 B1 | 5/2003 | Pommer | 257/731 |
| 6,583,630 B2 | 6/2003 | Mendes et al. | 324/652 |
| 6,600,404 B1 | 7/2003 | Kajino | 336/200 |
| 6,606,022 B1 | 8/2003 | Taurand | 336/200 |
| 6,608,545 B2 | 8/2003 | Fricker et al. | 336/200 |
| 6,665,931 B2 | 12/2003 | Yamaguchi et al. | 29/850 |

(Continued)

*Primary Examiner*—Anh Mai
(74) *Attorney, Agent, or Firm*—Michael C. Soldner; Carol F. Barry; Girma Wolde-Michael (57) ABSTRACT

Method and apparatus are provided for fabricating a planar transformer assembly for use in an implantable medical device. The planar transformer assembly includes a board, a first core, and a second core. The board has a first side, a second side, and an embedded winding, wherein the embedded winding includes a primary winding and a secondary winding and is at least partially embedded in the board between the first and second sides.

9 Claims, 9 Drawing Sheets

U.S. PATENT DOCUMENTS

| | | | |
|---|---|---|---|
| 6,727,793 B2 | 4/2004 | Piechnick | 336/198 |
| 6,794,977 B2 | 9/2004 | Christensen | 336/200 |
| 2001/0042905 A1 | 11/2001 | Katzir et al. | 257/666 |
| 2003/0132825 A1 | 7/2003 | Gamou | 336/223 |
| 2003/0179067 A1 | 9/2003 | Gamou et al. | 336/223 |
| 2003/0197256 A1 | 10/2003 | Pommer | 257/678 |
| 2004/0027224 A1 | 2/2004 | Giandalia et al. | 336/200 |
| 2004/0074086 A1 | 4/2004 | Yamaguchi et al. | 29/745 |
| 2004/0130913 A1 | 7/2004 | Giandalia et al. | 363/16 |
| 2004/0145445 A1 | 7/2004 | Yang | 336/223 |
| 2004/0174241 A1 | 9/2004 | He et al. | 336/200 |

* cited by examiner

INTEGRATED PLANAR FLYBACK TRANSFORMER

FIELD OF THE INVENTION

The present invention generally relates to medical devices, and more particularly to a transformer for use in an implantable defibrillator.

BACKGROUND OF THE INVENTION

An implantable medical device (IMD) such as an implantable cardioverter defibrillator (ICD) may be used to deliver shock therapy to a patient's heart in order to perform therapies such as defibrillation and cardioversion. Some ICDs may also provide several different pacing therapies, including such therapies as cardiac resynchronization, depending upon the needs of the user or patient and the medical condition of the patient's heart. For convenience, all types of implantable medical devices will be referred to herein as IMDs, it being understood that the term, unless otherwise indicated, is inclusive of an implantable device capable of administering any one of a number of cardiac therapies.

Typically, an IMD is implanted in a convenient location usually under the skin of a patient in the vicinity of one or more major arteries or veins. One (or more) electrical leads connected to the IMD is endocardially placed, usually through a convenient vein or artery. The ends of the leads are placed in contact with the walls or surface of one or more chambers of the heart, depending upon the particular therapy deemed appropriate for the patient.

One or more of the leads is adapted to carry a current from the IMD to the heart tissue to stimulate the heart in one of several ways, again depending upon the particular therapy being delivered. The leads are simultaneously used for sensing the physiologic signals provided by the heart to determine when to deliver a therapeutic pulse to the heart, and the nature of the pulse; e.g., a pacing pulse or a defibrillation shock. Such IMDs are typically housed in a container or can that is made of metal or some other conductive material.

In IMDs that deliver defibrillation or cardioversion therapies, it is necessary to develop high voltages, perhaps 750 volts or more, within the IMD in order to administer a sufficient shock to a patient to correct an arrhythmia or a fibrillation, particularly a ventricular fibrillation. To generate such high voltages, a battery and capacitors (usually two) may be used. Preferably, the capacitors are fully charged before defibrillation or cardioversion therapies are delivered. In some configurations, flyback and non-flyback transformers are employed to incrementally charge the defibrillation capacitors prior to therapy delivery. Once the capacitors are charged, the defibrillation or cardioversion therapy is delivered via insulated gate bipolar transistors or other suitable semiconductor switches that are switched on and off to apply charge stored in the capacitors in biphasic pulse waveform to the heart.

Because IMDs are implanted subcutaneously, it is preferable that the IMD is sized as small as possible to reduce any discomfort that the patient may experience post-implantation. Conventionally, however, some of the electronic components that are housed within the IMD are relatively large. For example, transformers are used which have coil and core members that are physically separate from other IMD components. Although these conventional transformers have been reliable, they consume a considerable amount of space within the IMD.

Accordingly, it is desirable to provide a method and apparatus for reducing the volume of an implantable medical device. In addition, it is desirable to decrease the size of a transformer for use in an implantable medical device, while maintaining its reliability. Furthermore, other desirable features and characteristics of the present invention will become apparent from the subsequent detailed description and the appended claims, taken in conjunction with the accompanying drawings and the foregoing technical field and background.

BRIEF SUMMARY OF THE INVENTION

According to an aspect of the invention, there is provided a method for fabricating a planar transformer assembly for use in an implantable medical device. The planar transformer assembly includes a board, a first core, and a second core, the board having a first side, a second side, and an embedded winding, wherein the embedded winding includes a primary winding and a secondary winding and is at least partially embedded in the board between the first and second sides. The method includes the steps of bonding the first core to the board first side proximate the embedded winding and bonding the second core to the board second side proximate the embedded winding, wherein the embedded windings are disposed at least partially between the first core and the second core.

According to another aspect of the invention, there is provided a flyback transformer that includes a board, first and second embedded windings, and first and second planar cores. The board has a first side and a second side. The first and second embedded windings are disposed between said first and second sides. The first and second embedded windings each have a primary winding and a secondary winding adjacent said primary winding. The first and second planar cores are coupled to the board first side and board second side, respectively, and are each positioned such that each of said first and second embedded windings have a first section disposed between the first and second planar cores and a second section not disposed between said first and second planar cores.

According to still another aspect of the invention, there is provided a flyback transformer that includes a board, first and second embedded windings, and first and second planar cores. The board has a first side and a second side. The first and second embedded windings are disposed between said first and second sides. The first and second embedded windings, the first embedded windings having a primary winding and the second embedded winding having a secondary winding. The first and second planar cores are coupled to the board first side and board second side, respectively, and are each positioned such that each of said first and second embedded windings have a first section disposed between the first and second planar cores and a second section not disposed between said first and second planar cores.

BRIEF DESCRIPTION OF THE DRAWINGS

The present invention will hereinafter be described in conjunction with the accompanying drawings, wherein like reference numerals denote like elements.

DETAILED DESCRIPTION OF THE INVENTION

The following detailed description is merely exemplary in nature and is not intended to limit the invention or the application and uses of the invention. Furthermore, there is no intention to be bound by any expressed or implied theory presented in the preceding discussion or the following detailed description.

Figure 1:
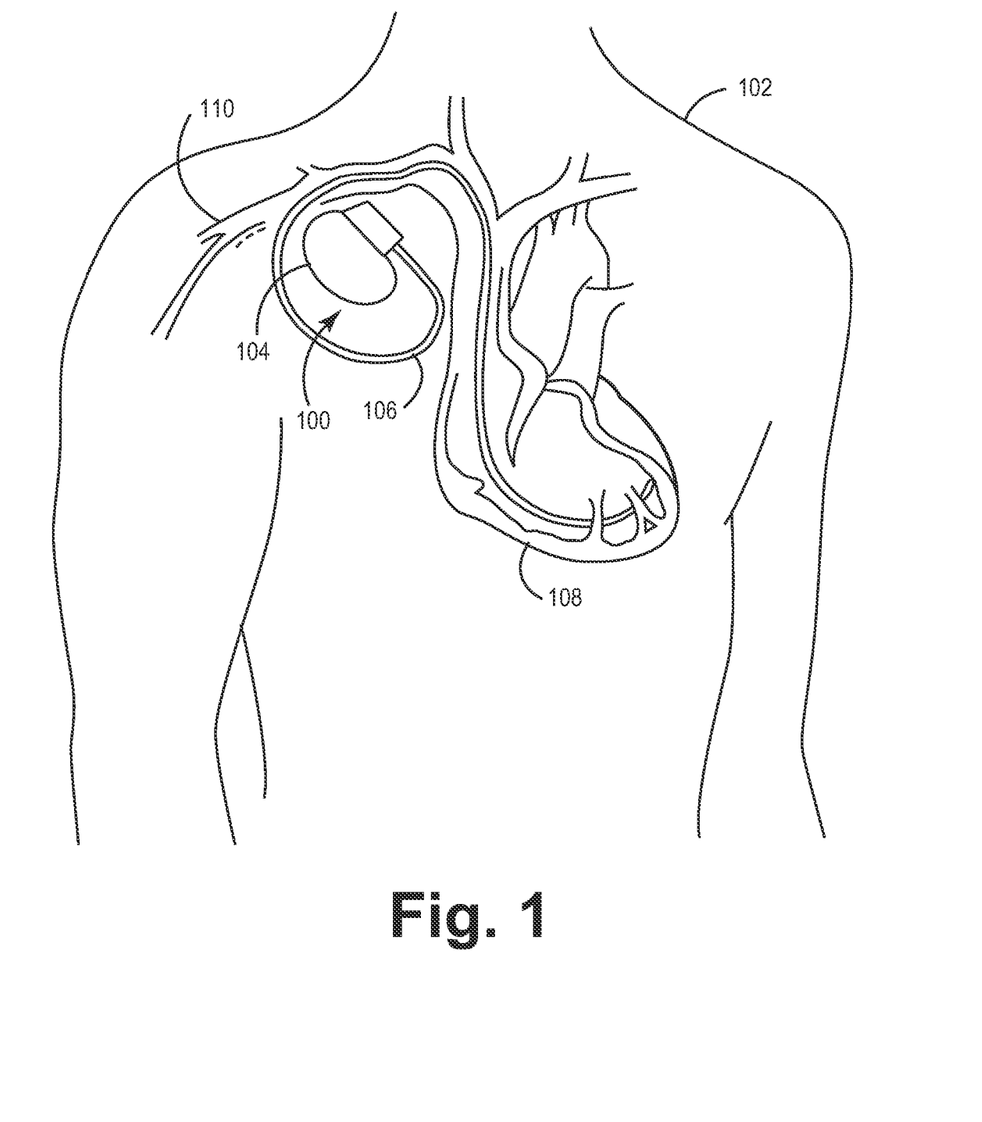
FIG. 1 is a diagram showing a typical placement of an IMD in a user.

FIG. 1 is an illustration showing generally where an implantable cardiac device (IMD) 100 is placed in a conventional manner in a patient 102. IMD 100 is conventionally housed within a hermetically sealed, biologically inert outer canister 104, which itself may be of a conductive material and serve as an electrode. One or more leads 106 are electrically coupled to IMD 100 in a conventional manner, extending into the patient's heart 108 via a vein 110. Disposed generally near the distal end of lead 106 are one or more exposed conductive electrodes for receiving electrical cardiac signals and/or for delivering electrical stimuli or other therapies to heart 108. Lead 106 may be implanted with its distal end in either the atrium or the ventricle of heart 108. Lead 106 is preferably a bipolar lead such that lead 106 actually has two separate and mutually insulated leads, the first having a terminal at the distal end of lead 106 and the second having a terminal near, but set back from the distal end. Such leads are well known in the art.

Figure 2:
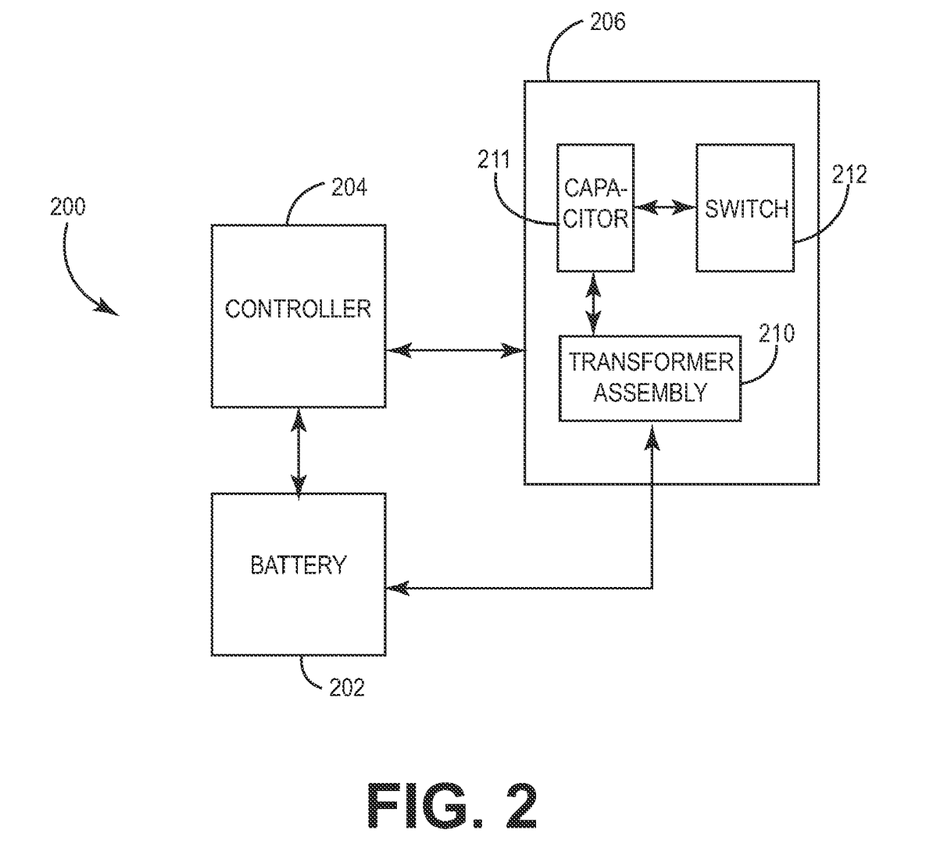
FIG. 2 is a simplified block diagram of a portion of circuitry that may be implemented within the IMD of FIG. 1.

FIG. 2 provides a simplified block diagram of exemplary circuitry 200 that may be housed within the canister 104 and is configured to produce pulses that are used to pace the heart; i.e., cause a depolarization of the heart tissue or issue a defibrillation pulse to shock the heart from arrhythmia to a normal heart beat. Circuitry 200 is shown to include a battery 202 electrically coupled to a controller 204 and a shocking circuit 206. Although circuitry 200 includes three components, it will be appreciated that fewer or more components may be employed. Battery 202 is configured to provide operating power to controller 204 and shocking circuit 206 and is preferably capable of operating at low current drains over a long duration and at high current pulses when shock delivery to patient 102 is required. Any one of numerous types of appropriate batteries may be used, such as, for example lithium/silver vanadium oxide batteries.

Controller 204 controls the delivery of energy through lead 106 (shown in FIG. 1). Controller 204 is preferably configured to determine when, where, and for what duration the energy may be delivered. In this regard, any one of numerous types of suitable control circuitry, such as microprocessors; or circuitry including memory, logic and timing circuitry; and I/O circuitry, may be employed.

Shocking circuit 206 is configured to generate low or high energy shocking pulses and to deliver the shocking pulses to patient 102 in response to control signals from controller 204. In this regard, shocking circuit 206 includes a transformer assembly 210 that is coupled to at least one capacitor 211, which is in turn coupled to a delivery switch 212. Transformer assembly 210 is configured to operate according to the principles of a flyback inductor, and thus, receives voltage from battery 202 to be converted to an appropriate voltage to be used by shocking circuit 206. The converted voltage is stored in capacitor 211, or any other suitable energy storage device, until the shocking pulse is ready to be delivered. When ready, delivery switch 212 is switched from an off position to an on position thereby routing the shocking pulse to the appropriate leads.

Figure 3:
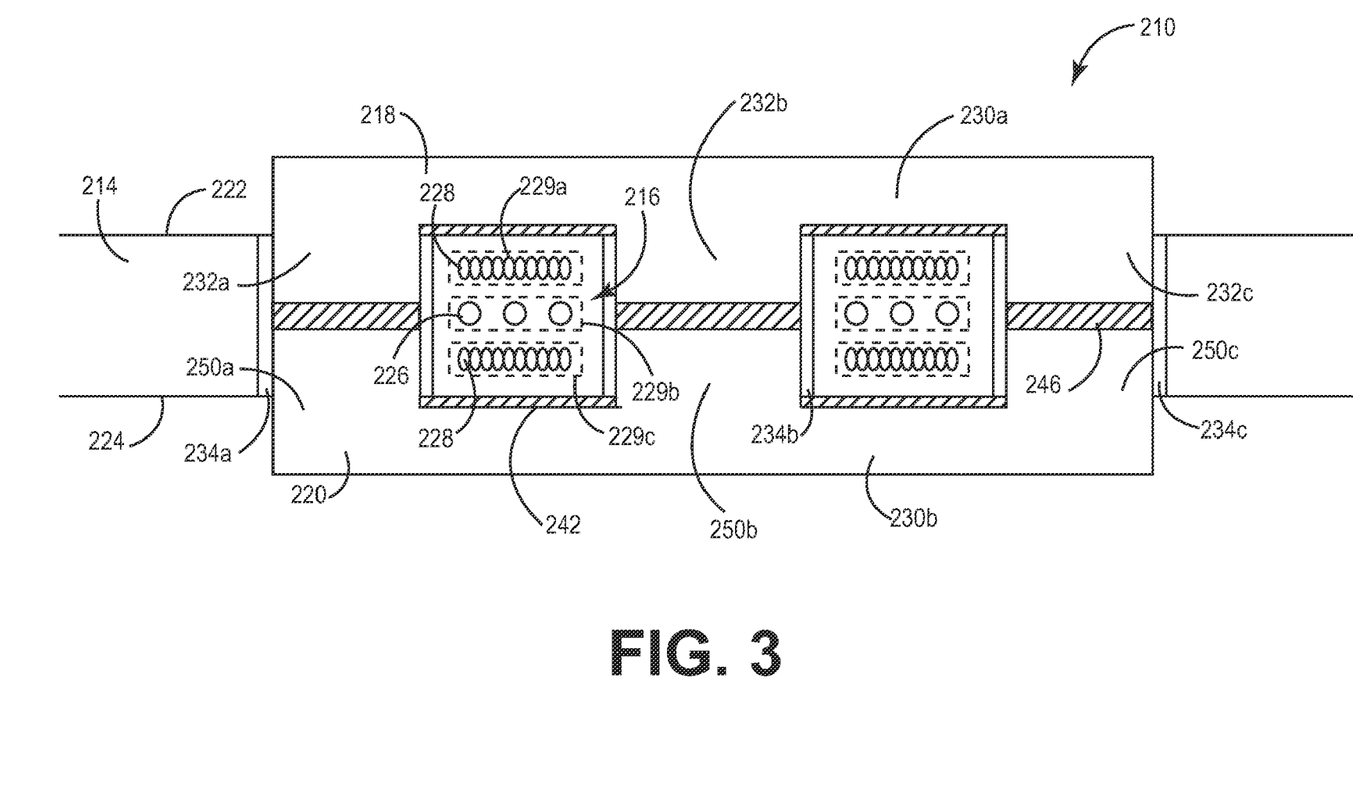
FIG. 3 is a cross-sectional view of an exemplary transformer assembly that may be used in the IMD of FIG. 1.

With reference to FIGS. 2 and 3, an exemplary transformer assembly 210 is illustrated. Transformer assembly 210 includes a board 214 within which windings 216 are disposed and onto which a first core 218 and a second core 220 are mounted. Board 214 has a first side 222 and a second side 224 and may include other circuitry printed thereon and other electronic components coupled thereto. To appropriately accommodate windings 216 and first and second cores 218, 220, board 214 is preferably a printed circuit board, a printed wiring board, but alternatively may be made of any other type of suitable substrate.

As depicted in FIG. 3, windings 216 are embedded between board first side 222 and second side 224. It will be appreciated that windings 216 may alternatively be coupled to first side 222 or to second side 224 or may be partially disposed between board first and second sides 222, 224 and also coupled to first side 222 or to second side 224. Windings 216 include a primary winding 226 and a secondary winding 228. Primary winding 226 is configured to receive the input voltage from battery 202, while secondary winding 228 is coupled to delivery switch 212 and capacitor 211. When the voltage input to primary winding 226 ceases and delivery switch 212 is in an on position, the voltage "jumps" to secondary winding 228. The received voltage is then stored in capacitor 211.

Figure 4:
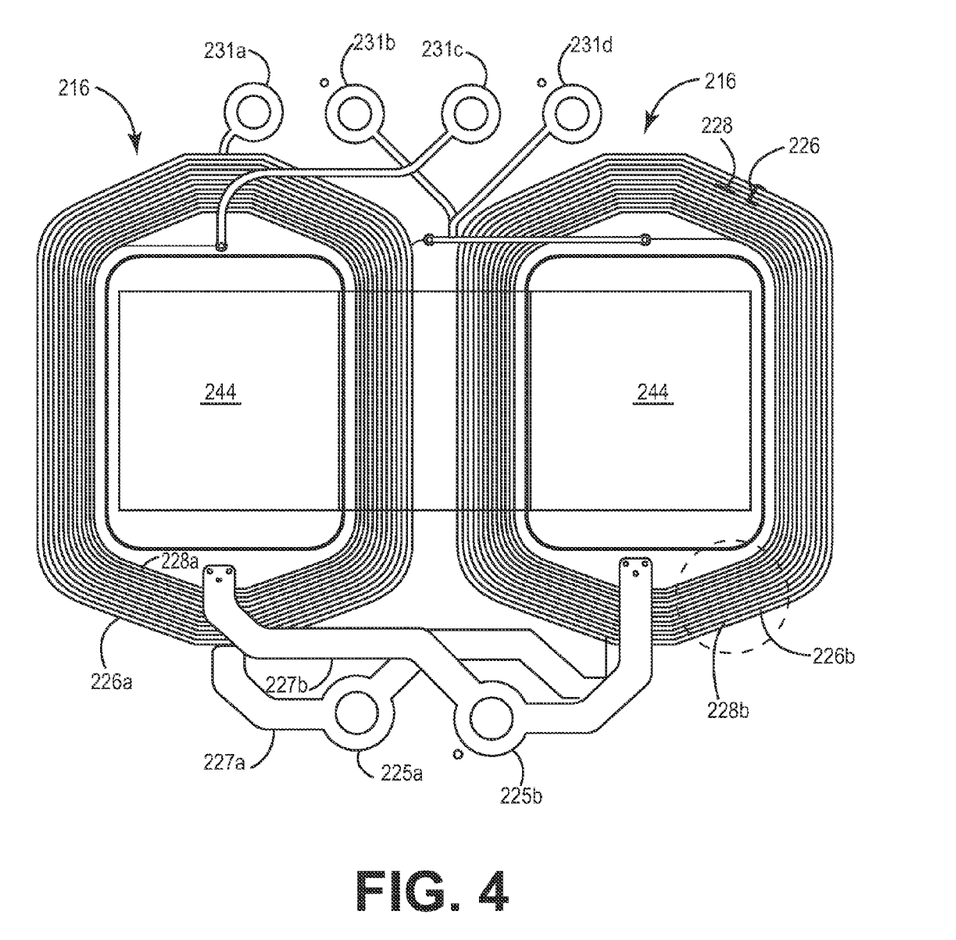
FIG. 4 is a top view of exemplary primary and secondary windings that may be employed in the IMD of FIG. 1.
Figure 5:
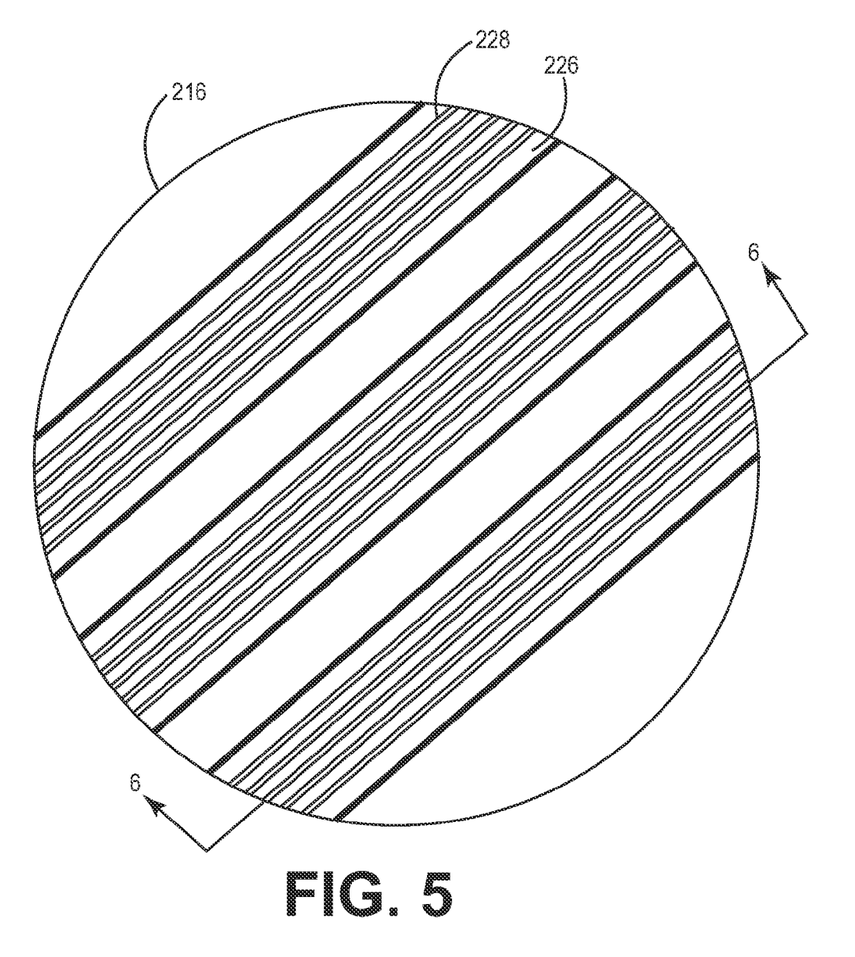
FIG. 5 is a close-up view of a portion of the exemplary primary and secondary windings depicted in FIG. 4.
Figure 6:
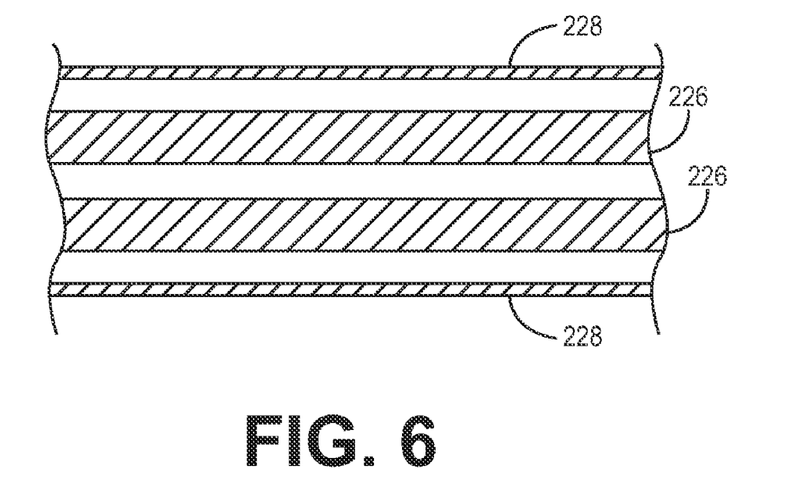
FIG. 6 is a cross-sectional view of the exemplary primary and secondary windings depicted in FIG. 5.

Turning to FIGS. 4, 5, and 6 a top view, a close-up view, and a cross-section view are provided of exemplary primary and secondary windings 226 and 228. Primary and secondary windings 226 and 228 are each wound around a space 244 located substantially in the middle of windings 226 and 228. It will be appreciated that although two sets each of primary and secondary windings 226a, 226b, 228a, and 228b are illustrated in FIG. 4, fewer or more may be employed. Each set of primary windings 226a and 226b are coupled to and are in parallel with one another via vias 227a and 227b. Vias 227a and 227b each include contact pads 225a and 225b, which are configured to communicate with other components of transformer assembly 210 and/or shocking circuit 206. Secondary windings 228a and 228b are each coupled to contact pads 231a, 231b, 231c, and 231d, which are also configured to communicate with other components of transformer assembly 210 and/or shocking circuit 206.

Each of primary windings 226 and secondary windings 228 has a number of turns formed therein. In order to achieve the desired voltage increase across transformer assembly 210, primary winding 226 preferably has fewer turns than secondary winding 228. When switch 212 is open and primary winding 226 receives current, energy continues to be stored between primary winding 226 and secondary winding 228 until a desired amount of energy is accumulated. When switch 212 is closed, secondary winding 228 directs the energy to capacitor 211. As will be appreciated, voltage in secondary winding 228 increases with each energy cycle. Parasitic reflected voltage to primary winding 226 is a function of the ratio of turns in windings 226, 228. Thus, if the ratio is 1:10, then secondary winding 228 is charged to 400 v and the parasitic reflected voltage to primary winding 226 is 40 v. In preferred embodiments, the ratio may be about 1:5 and 1:20.

Each of the windings 226 and 228 is contained on either individual or multiple layers of the board 214, such as illustrated in FIG. 3. In this exemplary configuration, board 214 includes a plurality of layers 229a, 229b, and 229c, and primary winding 226 is on a single layer, namely, layer 229b, while secondary winding 228 is on multiple layers, specifically, layers 229a and 229c. In an alternate embodiment, primary winding 226 may reside on one of layers 229a, 229b, or 229c, and secondary winding 228 may each reside another one of layers 229a, 229b, or 229c. In another exemplary embodiment, primary and secondary windings 226 and 228 are both located on one of layers 229a, 229b, or 229c. In still another embodiment, as illustrated in FIGS. 5 and 6, primary and secondary windings 226 and 228 are located on four layers 229a, 229b, 229c, and 229c. Here, secondary windings 228 reside on outer layers 229a and 229c and primary windings 226 reside on inner layers 229b, 229c. However, it will be appreciated that primary windings 226 and secondary windings 228 may have any other layering configuration.

Returning to FIG. 3, first core 218 and second core 220 are coupled to board 214 such that windings 216 are at least partially disposed between first and second cores 218 and 220. First and second cores 218 and 220 operate with windings 216 to generate a magnetic field when current is supplied to primary winding 226. In some configurations, first and second cores 218 and 220 may also be used to store magnetic energy when current supply to primary winding 226 ceases. Any one of a number of appropriate materials, may be used to construct first and second cores 218 and 220, such as, for example, a ferrite or a distributed gap core material, such as molypermalloy powder. First and second cores 218 and 220 are generally planar and may have any one of numerous shapes; however, it should be noted that the shape of first and second cores 218 and 220 may affect the configuration of board 214, and the number of windings 216 needed for proper operation of transformer assembly 210.

For example, in the embodiment illustrated in FIG. 3, first and second cores 218 and 220 are E-shaped and thus, each has a spine 230a, 230b and feet 232a, 232b, 232c, 250a, 250b, 250c that extend from its respective spine 230a, 230b. Feet 232a–c and 250a–c are each received by a first opening 234a, a second opening 234b, and a third opening 234c. Windings 216 are disposed around feet 232b and 250b so that the two may operate together to generate a magnetic field. First and second cores 218 and 220 are coupled to board 214 via a first bonding material 242, while feet 232a–c and 250a–c are bonded to one another via a second bonding material 246. In this embodiment, second bonding material 246 is preferably a conductive material. Likewise, first and second cores 218 and 220 are preferably constructed a conductive material, for example, ferrite.

Figure 7:
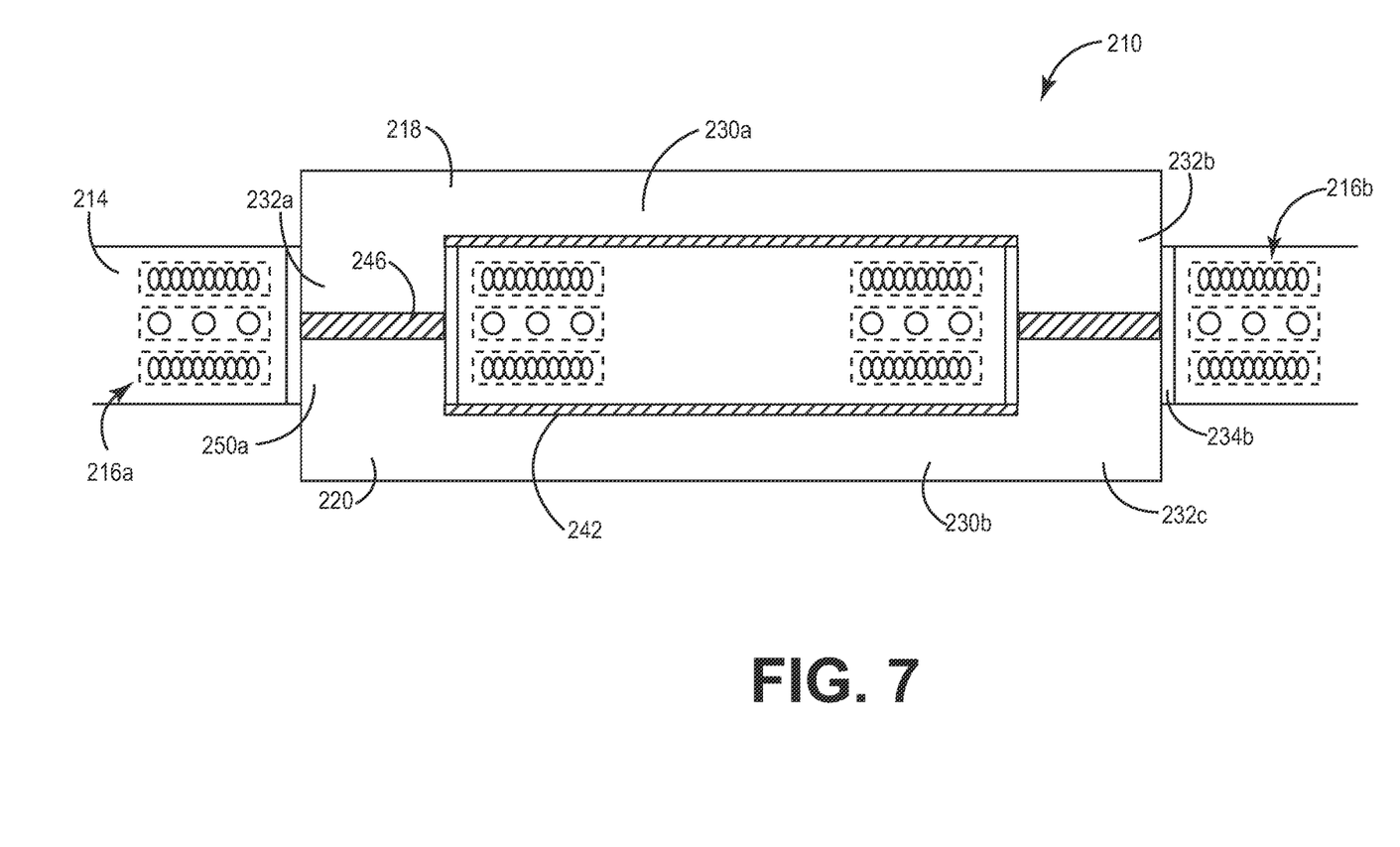
FIG. 7 is a cross-sectional view of another exemplary transformer assembly that may be used in the IMD of FIG. 1.

In another exemplary embodiment, first and second cores 218 and 220 are C-shaped, such as shown in FIG. 7. Similar to the above, first and second cores 218 and 220 each include a spine 230a, 230b, are bonded to board 214 with first bonding material 242 and are bonded to each other with second bonding material 246. However, in this embodiment, two feet 232a 232b, 250a, and 250b extend from spines 230a, 230b, instead of three feet, and, accordingly, two openings 234a and 234b are included in board 214. Additionally, two windings 216a and 216b are implemented and each is wound around the two feet 232a, 232b, 250a, and 250b. To allow windings 216a and 216b and cores 218 and 220 to properly operate, second bonding material 246 and first and second cores 218 and 220 are preferably non-conductive material. For example, second bonding material 246 may be epoxy or any other adhesive resin, while cores 218 and 220 may be constructed of distributed gap material.

Figure 8:
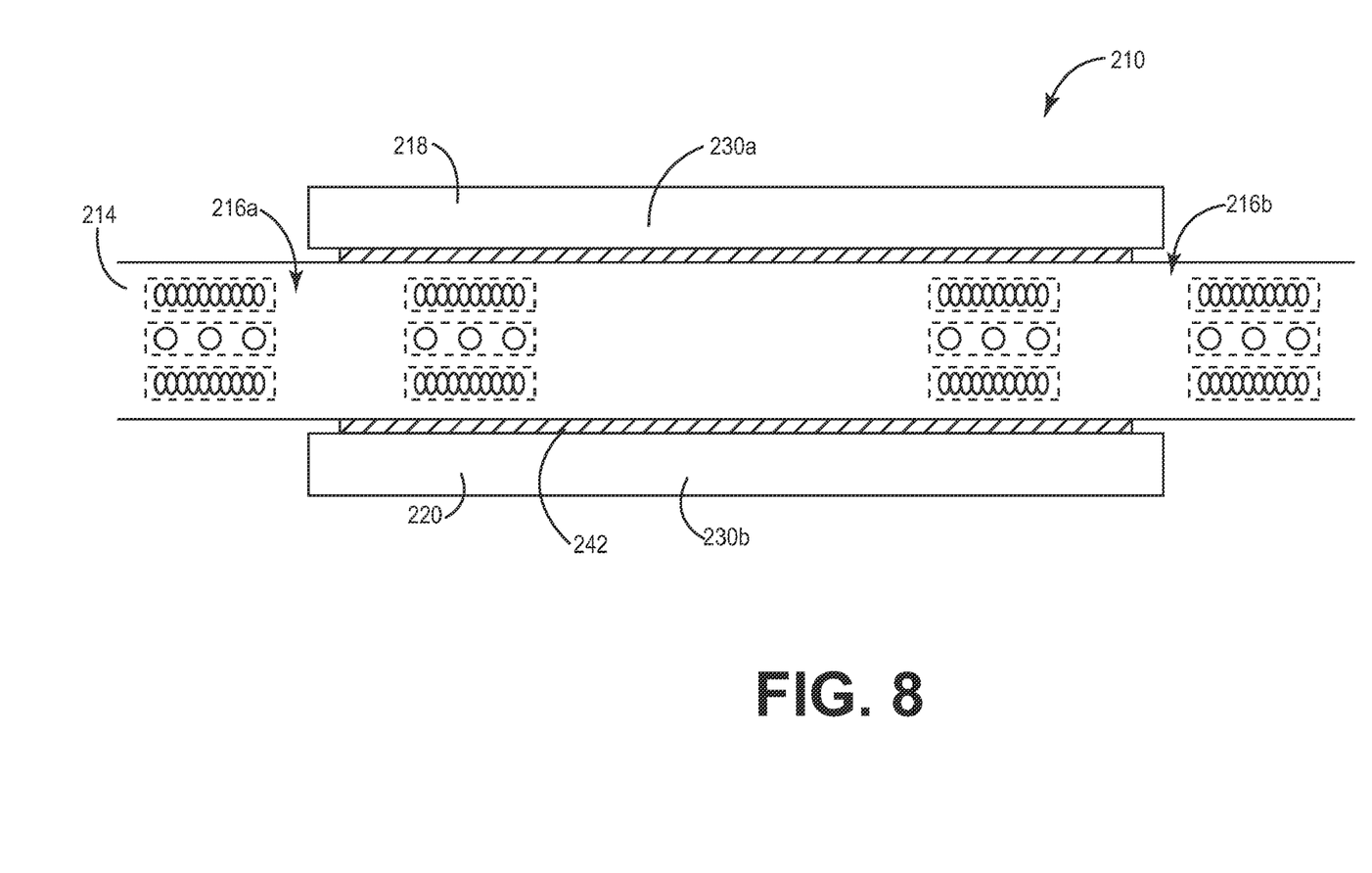
FIG. 8 is a cross-sectional view of still another exemplary transformer assembly that may be used in the IMD of FIG. 1.

In yet another example, such as illustrated in FIG. 8, first and second cores 218 and 220 are I-shaped. Thus, each of first and second cores 218 and 220 has a spine 230a and 230b and no feet. Similar to the C-shaped core example above, first and second cores 218 and 220 are bonded to board 214 via bonding material 242, and two sets of windings 216a and 216b are employed. However, in this embodiment, windings 216a and 216b are each embedded such that a portion of each of windings 216a and 216b are located between first and second cores 218 and 220 and a portion of each of windings 216a and 216b extends beyond first and second cores 218 and 220.

It will be appreciated that although first and second cores 218 and 220 are depicted as having the same shaped cores, such configurations are not necessary for operation. For example, an E-shaped or C-shaped core may be employed with an I-shaped core. It will further be appreciated that although E-shaped, C-shaped, and I-shaped cores are illustrated, cores having a fewer or more feet extending from a spine may be employed as well.

Figure 9:
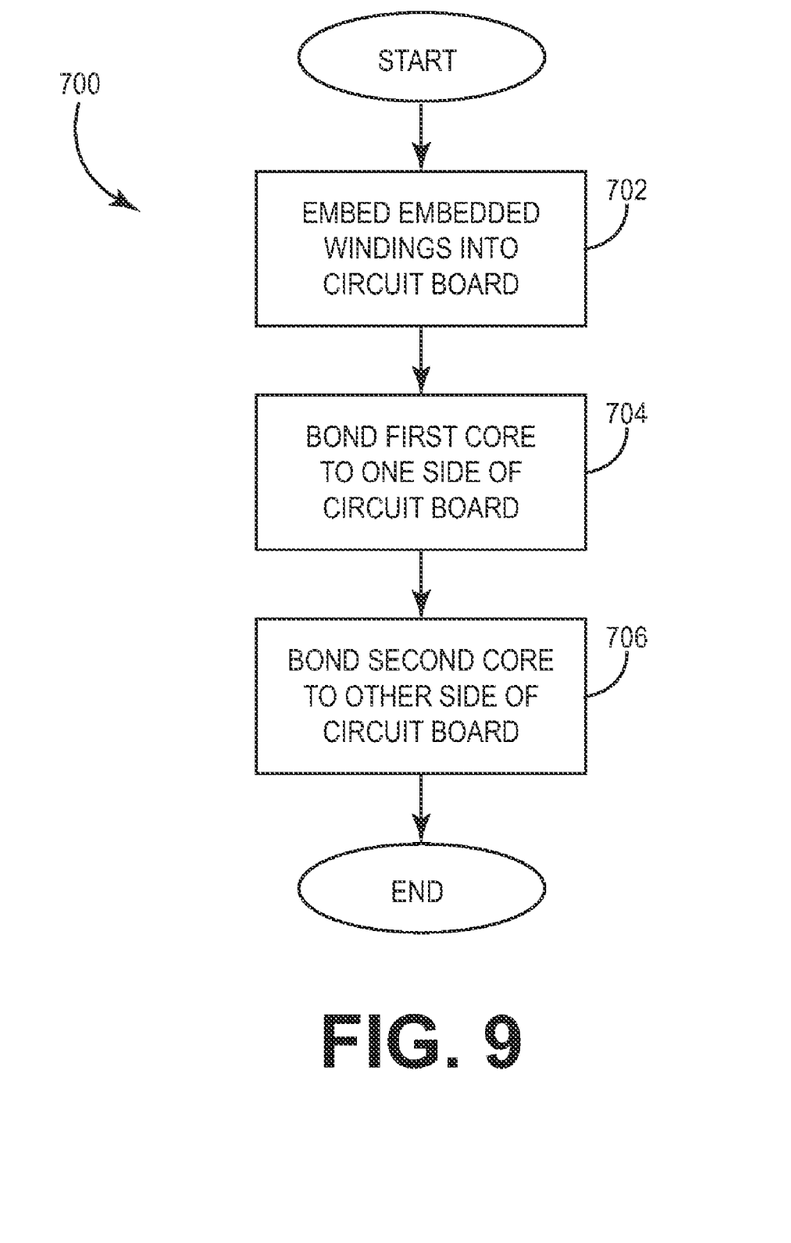
FIG. 9 is a flowchart depicting an exemplary method for assembling a transformer assembly.

FIG. 9 is a flowchart of an exemplary method (700) for fabricating the transformer assembly 210. Each step of the process (700) that is depicted in the flowchart is referenced herein by the use of parentheticals. First, windings 216 are embedded into board 214 (702). Then, first core 226 is bonded to board 214 (704). Next, second core 228 is bonded to board 214 (706). Each of these steps will now be discussed in detail.

As briefly mentioned above, windings 216 are first embedded into board 214 (702). Windings 216 may be embedded in board 214 using any one of a number of conventional manners. In one exemplary embodiment, windings 216 are conventionally printed onto a substrate and the printed substrate is then placed between two pieces of board material. In another exemplary embodiment, board 214 a space is disposed between board first side 222 and second side 224 and windings 216 are inserted into the space. In yet another exemplary embodiment, windings 216 are imbedded into board 214 during its manufacture.

Next, first core 226 is bonded to board 214 (704). The step of bonding first core 226 can include obtaining first core 226, preparing board 214 to receive first core 226, depositing bonding material 242 onto first core 226 and/or coupling first core 226 to board 214. First core 226 may be obtained via any one of numerous methods. For instance, first core 226 may be constructed from predetermined specifications, or first core 226 may be an off-the-shelf core. First core 226 may be pre-treated, for example, pre-tinned or pre-soldered in appropriate sections for future steps, or alternatively, may be bare.

As mentioned above, first core 226 may be any one of numerous shapes. If the first core 226 is E- or C-shaped, board 214 is preferably prepared for receiving first core 226. In this regard, an appropriate number of openings 234 that coincide with space 244 in the middle of windings 216 are formed through board 214. Openings 244 are sized to receive first core feet 232. In order to bond first core 226 to board 214, first bonding material 242 is deposited onto first core spine 230. As briefly mentioned in the description above, any type of appropriate bonding material, for example, non-conductive material, such as, adhesive, epoxy, and/or conductive material, such as solderable metal. The bonding material may be deposited in any conventional manner, such as by sputtering or vapor deposition.

After first bonding material 242 is properly applied to spine 230, first core 226 is placed against board 214 and an appropriate amount of pressure is applied to first core 226 to cause bonding. It will be appreciated that in the case in which first core 226 has feet 232, feet 232 are inserted into openings 234 before first core 226 is placed against board 214.

In another exemplary embodiment, openings 234 in board 214 are filled after first core 226 is bonded to board 214. In one example, a filler material is deposited into openings 234 after first core feet 232 are inserted therein. In another example, first core feet 232 include radial extensions that are sized larger than openings 234 so that first core feet 232 cover openings 234. In still another embodiment, a sealing gasket is coupled to openings 234.

It will be appreciated that other steps may be incorporated in to step 704. For example, an overmold may be deposited onto the board 214 after the first core 226 is bonded onto the board 214. The overmold may be any one of numerous materials that may serve as a protective coating for the board first side 222. In another example, an encapsulant is deposited onto the board 214 after the first core 226 is bonded onto the board 214. The overmold and/or encapsulant may be applied to either or both sides of board 214.

After first core 226 is bonded to board 214, second core 228 is then bonded to board 214 (706). This step may include obtaining second core 228, depositing second bonding material 246 onto second core 228, and coupling second core 228 to board 214. Second core 228 may be obtained in any manner, similar to those methods discussed above. Just as with first core 226, second core 228 may be pretreated, for example, pre-tinned or pre-soldered, or may be bare. Second core 228 may also have any one of numerous shapes and may include feet 250; however, the choice of shape may be dependent on whether a manufacturer desires to construct an E-E core, an E-I core, a C-C core, a C-I core, or an I-I core. After an appropriately shaped second core 228 is obtained, second bonding material 246 is deposited thereon. Any one of numerous bonding materials may be deposited onto second core 228, for example, any type of non-conductive material, such as, adhesive, epoxy, and/or conductive material, such as solderable metal.

In one exemplary embodiment, second bonding material 246 is deposited onto spine 230 of second core 228. In the case in which either first core 226 and/or second core 228 is pre-treated, second bonding material 246 may optionally be deposited on second core 228. After second bonding material 246 is deposited, second core 228 is coupled to board 214. Second core 228 may be coupled in any one of numerous manners. In one exemplary embodiment, spine 230 of second core 228 is placed directly onto board 214 and an appropriate amount of pressure is applied to cause second core 228 to adhere to board 214. In another exemplary embodiment, second core 228 includes feet 250. In such case, second core feet 250 are appropriately aligned with first core feet 232 and the feet 250, 232 are subsequently contacted to one another. In one exemplary embodiment, first core feet 232 are deposited with bonding material; thus, second core feet 250 are merely placed in contact with first core feet 232. In another exemplary embodiment, first core feet 232 are not deposited with bonding material; thus, bonding material is deposited onto second core feet 250 and the feet 232, 250 are contacted to one another. In still yet another exemplary embodiment, spine 230 is bonded to board 214 and feet 250 are adhered to first core feet 232.

Just as above, it will be appreciated that other steps may be incorporated in to step 706. For example, an overmold or encapsulant may be deposited onto the board 214 after the second core 228 is bonded onto the board 214. The overmold and/or encapsulant may be applied to either or both sides of board 214.

It will be appreciated that the method (700) described above may be implemented into an assembly of the electrical circuitry of transformer assembly 210. In such an embodiment, as cores 226, 228 are bonded to board 214, other circuits and/or circuit dye may be simultaneously deposited onto board 214. In other embodiments, the method (700) is implemented in a process for the manufacturing of only the transformer assembly.

Thus, a method and apparatus have now been provided that reduce the volume of an implantable medical device. In addition, the size of a transformer has been decreased for use in an implantable medical device, while maintaining its reliability.

While at least one exemplary embodiment has been presented in the foregoing detailed description, it should be appreciated that a vast number of variations exist. It should also be appreciated that the exemplary embodiment or exemplary embodiments are only examples and are not intended to limit the scope, applicability, or configuration of the invention in any way. Rather, the foregoing detailed description will provide those skilled in the art with a convenient roadmap for implementing an exemplary embodiment or exemplary embodiments. It should be understood that various changes can be made in the function and arrangement of elements without departing from the scope of the invention as set forth in the appended claims and the legal equivalence thereof.

What is claimed is:

1. A flyback transformer for use in an implantable medical device comprising:
   a board having a first side and a second side, the board comprising circuitry for delivering shocking pulses;
   a first and a second embedded winding disposed between said first and second sides, said first and second embedded windings each having a primary winding and a secondary winding adjacent said primary winding;
   a first and a second planar core coupled to said board first side and board second side, respectively, and positioned such that each of said first and second embedded windings includes a first section disposed between said first and second planar cores and a second section disposed between other than said first and second planar; and
   a set of contacts for electrically coupling said first and second embedded windings to the circuitry.

2. The planar transformer of claim 1, wherein said primary and secondary winding each have a number of turns and a turn ratio between the number of primary winding turns and the number of secondary winding turns.

3. The planar transformer of claim 2, wherein the turn ratio is between about 1:5 and 1:20.

4. The planar transformer of claim 1, wherein said board is one of a printed board and a printed wiring board.

5. The planar transformer of claim 1, wherein said embedded winding further comprises a layer and said primary winding and secondary winding are disposed on said layer.

6. The planar transformer of claim 1, wherein the embedded winding further comprises a plurality of layers and said primary winding and secondary winding are disposed on different one of said plurality of layers.

7. The planar transformer of claim 6, wherein said secondary winding is disposed on multiple layers of said plurality of layers.

8. A flyback transformer for use in an implantable medical device comprising:
- a board having a first side and a second side, the board comprising circuitry for delivering shocking pulses;
- a first and a second embedded winding disposed between said first and second sides, said first embedded windings having a primary winding and said second embedded winding having a secondary winding;
- a first and a second planar core coupled to said board first side and board second side, respectively, and positioned such that each of said first and second embedded windings includes a first section disposed between said first and second planar cores and a second section disposed between other than said first and second planar; and
- a set of contacts for electrically coupling said first and second embedded windings to the circuitry.

9. An implantable medical device, comprising:
- a board having a first side and a second side, said board comprising circuitry for delivering shocking pulses;
- a flyback transformer coupled to the circuitry wherein said flyback transformer comprises:
  - a first and a second embedded winding disposed between said first and second sides, said first embedded windings having a primary winding and said second embedded winding having a secondary winding;
  - a set of contacts for electrically coupling said first and second embedded windings to the circuitry;
  - a first and a second core coupled to said board first side and board second side, respectively, and positioned such that each of said first and second embedded windings includes a first section disposed between said first and second planar cores and a second section disposed between other than said first and second planar cores; and
- an encapsulant covering at least one of said first core and said second core;
- wherein said first core comprises a first spine and a first foot extending from said first spine;
- wherein said board comprises an opening for receiving said first foot, said first foot being conductively bonded to said second core.

* * * * *